US008083991B1

(12) United States Patent
Nassar

(10) Patent No.: US 8,083,991 B1
(45) Date of Patent: Dec. 27, 2011

(54) METHOD FOR DECONTAMINATING A BEAUTY CENTER

(76) Inventor: Roula Nassar, Houston, TX (US)

( * ) Notice: Subject to any disclaimer, the term of this patent is extended or adjusted under 35 U.S.C. 154(b) by 828 days.

(21) Appl. No.: 11/864,646

(22) Filed: Sep. 28, 2007

(51) Int. Cl.
    *A61L 2/00* (2006.01)
(52) U.S. Cl. .......................................................... 422/1
(58) Field of Classification Search ........................ 422/1
    See application file for complete search history.

(56) References Cited

U.S. PATENT DOCUMENTS

| 5,275,668 A * | 1/1994 | Dell et al. ........................ 134/10 |
| 2008/0163440 A1* | 7/2008 | Ruelas ........................... 15/21.1 |
| 2008/0166261 A1* | 7/2008 | O'Keefe et al. ................. 422/26 |

OTHER PUBLICATIONS

California State Senate Bill No. AB 1263 on Barbering and cosmetology: equipment, 2005.*
International Nail Technicians Association Guideline for Cleaning and Disinfecting Manicuring and Enhancement Equipment, Jan. 2007.*
International Nail Technicians Association Guidelines for Controlling and Minimizing Inhalation Exposure to Nail Products, Jan. 2007.*
International Nail Technicians Association Guidelines for Controlling and Minimizing Skin Exposure to Nail Products, Jan. 2007.*

* cited by examiner

*Primary Examiner* — Kevin Joyner
(74) *Attorney, Agent, or Firm* — Michael L. Parks

(57) ABSTRACT

A method for decontaminating a beauty center consisting of a protocol requiring the sanitation and disinfection of beauty tools, equipment and surfaces in a beauty center and using a decontamination center for decontaminating soiled non-disposable beauty tools. The method includes the protocol prohibiting "double dipping" with products in a beauty center; using a deep-cleaning agent to remove biofilm and using disposable beauty tools in conjunction with non-disposable beauty tools. The method reduces or eliminates the potential for the cross-contamination of communicable diseases in a beauty center.

18 Claims, 13 Drawing Sheets

METHOD FOR DECONTAMINATING A BEAUTY CENTER

FIELD

The present embodiments relate generally to a comprehensive, hospital-grade method for decontaminating a beauty center.

BACKGROUND

There exists a need for a comprehensive, hospital-grade method for ensuring the proper and effective decontamination of an entire beauty center including beauty tools, equipment and surfaces in a beauty center. The method consists of the following decontamination practices: sanitation, disinfection, sterilization, the prohibition of double-dipping, the use of a deep cleaning agent to remove biofilm and the use of disposable beauty tools. The method reduces or eliminates the potential for the cross-contamination of communicable diseases in a beauty center. The method can help stop the spread of transmittable diseases.

The present embodiments meet these needs.

BRIEF DESCRIPTION OF THE DRAWINGS

The detailed description will be better understood in conjunction with the accompanying drawings as follows.

Figure 1:
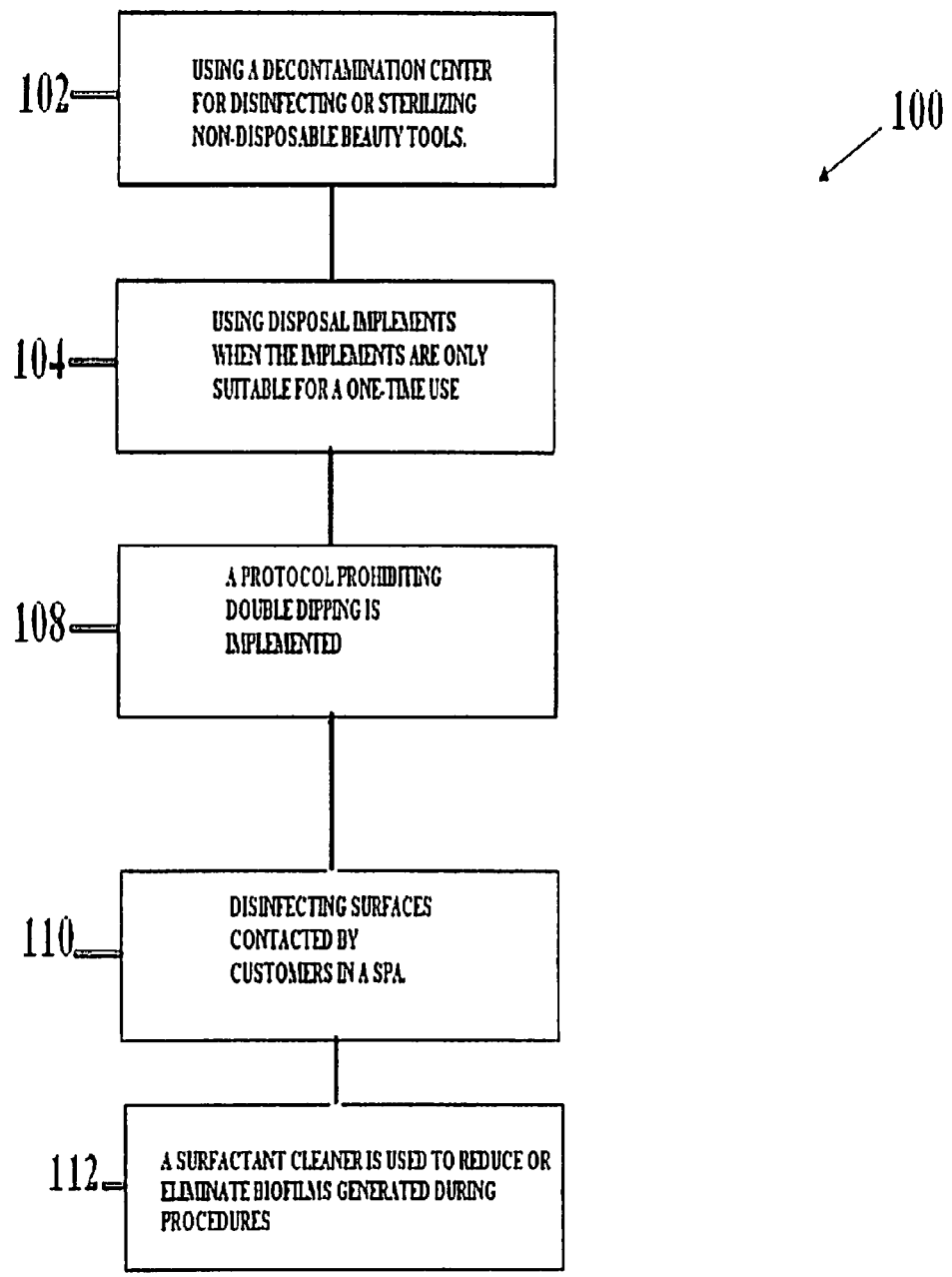
FIG. 1 depicts a flow diagram for an embodiment of the method.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments and that they can be practiced or carried out in various ways.

The salon and spa industry experienced moderately healthy growth levels until the 1970s, at which time salon and spa treatments were considered an upscale commodity and were accessible primarily to Hollywood starlets, European fashionistas and members of the elite social classes. The proliferation of discount salons and spas occurred in the 1970s as the industry began to target a new pool of mid- to lower-income clients. These discount facilities have become a catalyst for industry growth since the 1970s.

This increase in consumer demand was met by a significant increase in supply. Despite the salon and spa industry's strong growth levels, it has been suffering from poor education, lax laws regarding sanitary practices, poor governmental regulation and enforcement, low regulatory compliance rates and low market standards. Salon and spa personnel are rarely provided with adequate training or resources to maintain a sanitary environment. Most technicians are not owners and therefore not motivated to have sanitary environments.

In addition, many industry manufacturers fail to properly train industry personnel regarding the proper sanitation of their beauty tools and equipment on the basis that they are selling to licensed individuals who have already received the adequate training necessary to obtain their license. This assumption is often incorrect since industry personnel typically receive little education and training relating to sanitation, infectious diseases and the proper use of equipment per manufacturer guidelines.

During the last decade, sanitary issues have gained importance due, in part, to public safety issues, increased media coverage and a higher incidence of reported cases of cross-contamination of infectious diseases arising out of the unsanitary practices of salons and spas.

The term beauty center refers to a salon or spa that performs beauty and cosmetic treatments. Beauty centers can be stand-alone facilities or they can be located in shopping centers, cruise ships, hotels, resorts, airports and similar locations. Beauty centers are heavily concentrated in shopping centers and strip malls in major metropolitan cities. The following cases highlight situations in which patrons contracted a medically detrimental condition arising out of unsanitary practices at a beauty center.

There have been numerous outbreaks of mycobacteria fortuitum arising out of unsanitary practices at salons across the country during the last seven years. The first outbreak was identified in California; however, similar cases have been reported in South Carolina, Illinois, Arizona, Virginia, New York, San Diego, Los Angeles, Sacramento, Texas, Florida, Washington D.C. and Georgia. Some of these documented outbreaks included multiple people, while others involved only a few. It is not possible to chronicle all of the reported cases, particularly since many of them are still under investigation; however, the following identify some of the major outbreaks.

In October of 2000, over 100 people were infected by an outbreak of mycobacteria fortuitum from the Fancy Nails salon in northern California. All of the clients had received pedicures that left them with prolonged boils on their legs, which ultimately left permanent and disfiguring scars when they healed. This was the first major outbreak of its kind, as similar infections were typically previously witnessed in healthcare settings.

The outbreak prompted an investigation by the California Bureau of Barbering and Cosmetology, California Department of Health Services and Centers for Disease Control (CDC), wherein multiple environmental samples were taken from 30 whirlpool tubs in 18 nail salons from five counties in California and sent to the California Microbial Diseases Laboratory for analysis. Ten different species of Mycobacteria were isolated in the analysis, of which six were rapidly-growing mycobacteria (RGM), as is reflected in the chart below:

Findings of Mycobacteria by Species

| Mycobacteria | No. (%) of Spas |
|---|---|
| Mycobacterium Fortuitum* | 14 (47) |
| M. Mucogenicum* | 7 (23) |
| M/ Megeritense* | 6 (20) |
| M. Avium Complex | 5 (17) |
| M. Smegmitis Group* | 4 (13) |
| Unidentified Nontuberculosis Mycobacteria | 3 (10) |
| M. Simiae | 3 (10) |
| M. Gordonae | 2 (7) |
| M. Neoaurum-like* | 2 (7) |
| M. Lentiflavum | 2 (7) |

*Rapidly Growing
Source: Centers for Disease Control

According to Bohn & Bohn, LLP, affected patrons sued a nail salon, as well as associated manufacturers and suppliers of the pedicure stations. The plaintiffs were awarded a $2.91 million settlement resulting from the improper cleaning and disinfecting of the pedicure stations. During its analysis of the 2000 Santa Cruz outbreak, the CDC made the following statement:

"Nonetheless, our findings document the ubiquitous presence of potentially pathogenic mycobacteria among footspas of nail salons in California."

According to NBC News, in other outbreaks in 2003 and 2004, approximately 147 patrons alleged they contracted mycobacterial infections from 33 salons throughout the Santa Clara County, Calif. area. A lawsuit alleging negligence due to the improper cleaning and disinfecting of pedicure stations was brought against the implicated salons, as well as associated manufacturers and suppliers of the pedicure stations. The case is still open and under investigation.

A similar mycobacterial infection outbreak involving 17 salon patrons and at least five different nail salons took place in March 2005 in Contra Costa County, Calif. The case is still open and under investigation. Furthermore, two cases of the M. mageritense bacteria linked to pedicure stations at a nail salon in Georgia were reported to the CDC.

In another case, Jessica Mears contracted a mycobacterial infection from a pedicure she had received on Nov. 24, 2004 from the Top Hair and Nails salon in San Francisco, Calif. According to the San Francisco Chronicle, the infection was manifested as a 4 by 6 lesion on her left leg. Jessica suffered from Lupus, a chronic condition that suppresses the immune system, so she was unresponsive to her treatment, which consisted initially of antibiotics and then the surgical removal of the infected skin. The infection ultimately led to her death on Jun. 20, 2006. Diana Mears, her mother, filed a wrongful death lawsuit based on the salon's alleged negligence due to the improper cleaning and disinfecting of their pedicure stations. The case is still open and under investigation. These problems are severe when death results.

Based on an article in NBC News, Amber Witherow allegedly contracted a staph infection from an eyebrow wax she had received at a salon in Lancaster, Pa. in 2006. A few days after her treatment, she developed a methicillin-resistant staphylococcus aureus (MRSA) infection near her right eye, which became purple and swollen. She began to suffer other symptoms, including headaches, migraines and vomiting, and had to eventually be admitted to the hospital due to the severity of her symptoms. Amber was told that her illness could have been life-threatening had she waited one more day before seeking treatment in the hospital. Although her doctor was not able to determine conclusively that the infection was the result of a wax treatment, based on her symptoms and risk factors, the belief was that the wax caused the infection, which will likely take up to a year to heal. A need has existed to stop these illnesses at nail and foot salons.

In addition, on Nov. 16, 2006, Channel 6 News (KFDM) reported that a lady contracted a plantar wart infection on her feet after receiving an unsanitary pedicure at a Texas salon. The wart eventually spread to her hand, given that she used her finger to apply the medication on her feet and that warts are highly contagious.

A comprehensive, hospital-grade method of decontamination would have prevented all of the above-mentioned cases of cross-contamination. According to the CDC, decontamination involves the "use of physical or chemical means to remove, inactivate, or destroy pathogens on a surface or item so that they are no longer capable of transmitting infectious particles and the surface or item is rendered safe for handling, use, or disposal." There are three levels of decontamination: sanitation, disinfection and sterilization. The present invention uniquely presents all three levels for use in a manicure pedicure facility or other beauty center equipment.

Sanitation: The first and lowest level of decontamination, involves the physical removal of visible debris and microbes by washing hands, beauty tools or other surfaces using water and soap or a detergent. This results in a microbial reduction of 99.99%.

Disinfection: The second, or intermediate level of decontamination, is disinfection. It involves the use of chemicals to destroy pathogenic and other microorganisms; however, it does not eliminate all bacterial forms, such as bacterial spores.

Disinfection results in a microbial reduction of 99.999%, which is less than sterilization but more than sanitation.

Sterilization: The highest level of decontamination is sterilization, which involves the complete elimination of all microorganisms, including high numbers of bacterial spores.

An embodiment of the method of decontamination can reduce or eliminate all viral, bacterial and fungal microorganisms, as well as the potential for the cross-contamination of infectious diseases. Infectious diseases are human illnesses caused by microbes, parasites, fungi, bacteria and viruses. Industry insiders and public health officials warn that the potential for the cross-contamination of numerous infectious diseases in a salon and spa environment poses considerable health risks to consumers and operators who are occupationally exposed to infectious materials and disease-infected individuals. This is critical because, although the body has defenses to fight infection, when too many germs colonize in a particular area where they are not usually encountered, the risk of infection increases, even for healthy individuals who are not at-risk. Improper decontamination techniques can result in a myriad of viral, bacterial and fungal infections.

The viral microorganisms most likely to be transmitted while administering beauty center services include, but are not limited to, warts, herpetic whitlow (herpes infection) and various blood-borne pathogens, such as the human immunodeficiency virus (HIV), hepatitis B virus (HBV) and hepatitis C virus (HCV). Viral microorganisms can cause severe illness or, in some cases, death. They are eliminated by a comprehensive, hospital-grade method of decontamination.

The bacterial microorganisms most likely to be transmitted while administering beauty center services include, but are not limited to, *staphylococcus, streptococcus, mycobacteria* and *pseudomonas*. There is also evidence to suggest that bacterial spores can be spread through the use of beauty tools. Bacterial spores cannot be killed by the use of a chemical disinfectant; therefore, sterilization is required to ensure that bacterial spores are prevented from spreading throughout a beauty center. Bacterial microorganisms can cause severe illness or, in some cases, death. They are eliminated by a comprehensive, hospital-grade method of decontamination.

The fungal microorganisms most likely to be transmitted while administering beauty center services include, but are not limited to, onychomycosis, athlete's foot and similar fungi. Fungal microorganisms can cause severe illness or, in some cases, death. They are eliminated by a comprehensive, hospital-grade method of decontamination.

The embodiments of the invention relate generally to a method for decontaminating beauty tools, equipment and surfaces in a beauty center. The method can eliminate at least one of three types of microorganisms: viral, bacterial and fungal microorganisms.

The method for decontamination has many benefits. The method is designed in such a manner that it can be used in beauty centers, training centers and educational facilities where supervision may be lacking. The simple, straight forward way of using the method of decontamination is important because most beauty center operators have a rudimentary level of skills and education, especially in the areas of communicable diseases and sanitary practices. For example, approximately 25 percent of technicians have completed collegiate or graduate level studies. Furthermore, schooling requirements for cosmetology programs are generally low. Cosmetology schools offer little to no training in the fields of decontamination techniques or infectious diseases.

Furthermore, it is important to have an easy-to-use system for decontamination because several beauty center operators speak English as a second language, creating a language barrier, which makes it difficult to train beauty center operators on methods of decontamination. The embodiments of the method ensure that beauty tools, equipment and surfaces are substantially sanitized, disinfected and sterilized regardless of the education level of the beauty center technician implementing the method, which is designed to enable anyone to utilize it. The method for decontamination significantly increases the probability that discount beauty centers will remain sanitary.

There is very little governmental oversight regarding the sanitary practices of beauty centers. For example, California and Texas only have a dozen inspectors to patrol ten of thousands of salons and spas; as a result, each facility is inspected on average once every three to five years. When inspections are conducted, they are simply visual, meaning a lab specimen of the beauty center's tools is not taken to ensure beauty tools and surfaces have been properly decontaminated. This scenario is reflective of other state cosmetology boards nationwide, which are the industry's governing regulatory agencies. Furthermore, the lack of sanitary practices is prevalent in high- and low-end beauty centers. The present embodiments of the invention reduce the need for governmental oversight of facilities in all market segments by providing a way to ensure sanitary practices for beauty centers.

Although it is impossible to achieve sterility in a public environment, salons can implement certain infection-control practices to significantly reduce or eliminate the risk of cross-contamination of infectious diseases.

In an embodiment of the invention, the method creates a beauty center wherein beauty tools, equipment and surfaces are decontaminated properly and effectively based on the implementation of the following protocols: 1) the sanitation of all beauty tools, equipment and surfaces prior to being disinfected or sterilized, thereby increasing the efficacy (its ability to kill microorganisms) of the disinfection or sterilization process, 2) the disinfection of certain beauty tools, equipment and surfaces with a disinfection solution 3) the sterilization of certain soiled non-disposable beauty tools in a sterilization treatment unit in a decontamination center, 4) the prohibition of double-dipping into any products used during beauty treatments, 5) the use of disposable beauty tools used during beauty treatments that cannot be disinfected or sterilized, 6) the use of a deep cleaning agent to reduce or eliminate the build up of biofilm on beauty center equipment and 7) a set of other standard protocols called "rules" that consist of a number of hospital-grade standards of infection-control. This method of decontaminating a beauty center reduces or even eliminates the potential for customers and beauty center technicians to contract infectious diseases.

The first method of decontamination in a beauty center requires the sanitation of all beauty tools, equipment and surfaces prior to being disinfected or sterilized, thereby increasing the efficacy of the disinfection or sterilization process. The term beauty tool refers to the tools used in beauty centers while performing services.

Beauty tools can be porous or nonporous. Nonporous beauty tools include, but are not limited to, drill bits, one-cuts, nail clippers, scissors, nippers, metal pushers, extraction tools and combinations thereof. Porous beauty tools include, but are not limited to, buffers, nail files, foot files, abrasives, toe separators, pedicure shoes, cotton, orange wood sticks, wax applicators, lancets, callus rasps, natural pumice stones, foot brushes, arbor and sanding bands, sleeves, exfoliating blocks and combinations thereof.

One embodiment of the invention requires sanitation of beauty tools by physically removing visible debris by using a brush to scrub the debris off the tools with water and soap or a detergent. It should be noted that any beauty tools that are not disposed of after a service must be sanitized, or pre-cleaned, in between patrons.

An embodiment of the method requires the sanitation of equipment, such as a pedicure station, in a beauty center. In order to sanitize a pedicure station, water must be thrown away or drained from the tub. Then all visible debris must be physically removed from the basin by scrubbing its surface with water and soap or a detergent using a brush. The tub must then be rinsed with fresh clean water.

All surfaces in a beauty center must be sanitized on a regular basis daily. Sanitizing a surface consists of using a brush to physically remove visible debris by scrubbing the debris off the surface with water and soap or a detergent upon the completion of a service.

In an alternative embodiment, a surface can be sanitized by using a towel or napkin and applying water and soap or detergent to rub off any visible debris from the surface.

The second method of decontamination in a beauty center requires the disinfection of beauty tools, equipment and surfaces with a disinfection solution.

Certain beauty tools that are used on more than one person must be disinfected in between services with a hospital-grade disinfectant registered with the Environmental Protection Agency (EPA). Per the EPA's guidelines, EPA-registered disinfectants are for use strictly on hard, nonporous surfaces. While the typical microorganisms killed by a disinfectant include viral, bacterial and fungal microorganisms, the use of a tuberculocidal disinfectant can result in the elimination of additional microorganisms.

Upon completion of the sanitation process, nonporous beauty tools must be disinfected. This process consists of placing the nonporous beauty tools in a container filled with an EPA-registered disinfectant, wherein the objects are fully immersed for at least ten minutes, as is required for all EPA-registered disinfectants and per manufacturer guidelines. A contact period of less than ten minutes will prevent the appropriate and necessary eradication of microorganisms and reduce the efficacy of the disinfection process. Furthermore, the container must have a closed cover to prevent contamination of the disinfectant. EPA-registered disinfectants become inactivated and ineffective when visibly contaminated with debris, hair, dirt and particulates. Therefore, replacement of the disinfectant should occur when the solution becomes diluted or soiled per manufacturer guidelines.

In another embodiment, non-porous beauty tools and certain porous beauty tools made out of absorbent materials, such as nail files, buffers, pedicure files, callus rasps, natural pumice stones, foot brushes, arbor and sanding bands, sleeves, and exfoliating blocks, can be immersed in or sprayed with a 10% bleach solution (one part bleach to nine parts cold water) or 70% or higher isopropyl or ethyl alcohol. Once the beauty tools have been immersed for the necessary amount of time per manufacturer guidelines, they should be removed, wiped dry with a clean towel and stored in a dry storage container that is properly labeled.

The method requires that all equipment in a beauty center that is used on more than one patron be disinfected in between patrons. Equipment that can be disinfected in a beauty center can be a pedicure station.

It is a common practice for salon operators to simply throw away or drain water from a pedicure station and refill it with water without disinfecting the stations in between patrons. Some pedicure stations have internal piping systems, wherein water is re-circulated, creating a significant health hazard. Water can be a breeding ground for bacteria, fungi and viruses, and a medium through which pathogens can be transmitted. Water in a pedicure tub can be contaminated by one source. If pedicure stations are not disinfected properly in between guests, the same water can be re-circulated through the pipe lines and can contaminate other hosts. The surface of the stations can also harbor pathogens. Therefore, pedicures stations can result in the cross-contamination of viral, bacterial and fungal infections.

The following protocols pertain to the disinfection of a pedicure footbath with water in which clients place their feet. There are various types of pedicure stations, including whirlpool spa chairs, pipe-less spa chair units, basins, tubs, sinks and bowls. Upon completion of the sanitation process, the tub should be rinsed and filled with fresh water. Then an EPA-registered, hospital-grade disinfection solution should be mixed or diluted with the water per manufacturer guidelines to ensure proper disinfection. All EPA-registered disinfectants require a 10-minute contact period with a surface that is free of debris to ensure efficacy. A contact period of less than ten minutes will prevent the appropriate and necessary eradication of microorganisms and reduce the efficacy of the disinfection process. If the station is a whirlpool spa chair, the system should be flushed out by turning the jets on per the manufacturer guidelines. Doing so circulates the disinfection solution throughout the internal components of the spa chair. After the 10-minute time period has passed, the disinfection solution should be drained and the tub should be rinsed with fresh water. Finally, the basin should be dried with a clean towel.

In an alternative embodiment, the pedicure stations can be disinfected with a 10% bleach solution, wherein the pedicure basin can be filled with one part bleach and nine parts cold water, following the steps outlined in the previous paragraph.

The screens in pedicure stations must be disinfected daily. The screens should be removed from the pedicure stations every morning or at the end of each day. After undergoing the process of sanitation, they should be disinfected in an EPA-registered hospital-grade disinfectant. They should be fully immersed in the disinfection solution for 10 minutes in accordance with manufacturer guidelines. They should be rinsed with fresh water and dried with a clean towel. Then they must be screwed back into the pedicure station.

In an alternative embodiment, the screens can be fully immersed in 10% bleach solution (one part bleach to nine parts cold water) or 70% or higher isopropyl or ethyl alcohol for 5-10 minutes following the same steps outlined in the previous paragraph.

The method further includes using a disinfection solution to disinfect surfaces contacted by customers in the beauty center. The disinfectant can be an EPA-registered, hospital-grade disinfectant, such as Ameri-Kleen, which is manufactured by Amerikleen Corporation.

Environmental surfaces in a beauty center can become contaminated and can act as a breeding ground for microorganisms. Although it is unlikely that environmental surfaces would transmit an infection directly to a human, they can serve as a mode of transmission of microbial agents to beauty tools or other surfaces.

Certain blood-borne diseases can live on environmental surfaces for days. For example, according to the CDC, the HBV can live on environmental surfaces for at least seven days and can still be capable of causing infection, while HCV may survive on environmental surfaces for at least 16 hours, but no longer than four days at room temperature.

All hard, nonporous, surfaces that come into contact with people, such as manicure stations and manicure bowls should be disinfected in between patrons upon completion of the sanitation process. An EPA-registered, hospital-grade disinfectant should be sprayed onto a surface and must have a 10-minute contact time period before being rinsed and wiped off with a towel or napkin.

An embodiment of the method of decontamination requires the sterilization of soiled beauty tools in a sterilization treatment unit. While the proper and effective sanitation and disinfection of beauty tools eliminates 99.999% of microorganisms, it is recommended that all soiled non-disposable beauty tools be sterilized in a sterilization treatment unit in between clients. Human error can result with the immersion time period of beauty tools in a disinfection solution, the rate of solution replacement, improper mixing or diluting of chemical disinfectants, or other manual operations involved in disinfection. The decontamination center eliminates the amount of human error potentially experienced throughout the disinfection process because of the arrangement and flow process of the decontamination center, which enables the technician to rely on the equipment to carry out all necessary steps.

During the administration of beauty center procedures, it is possible to puncture or break the skin or nails of a client, which can cause blood and body fluids to contaminate beauty tools. Due to the associated risk, it is extremely important to ensure the proper and effective sterilization of beauty tools used during the treatment of patrons. Beauty tools can be sterilized between each patron of a beauty center.

Sterilization is critical for many reasons: 1) Due to a lack of education and training regarding infection-control protocols for industry professionals, effective measures, such as disinfection, are not being implemented properly at a unit level to ensure the safety of operators and consumers alike and 2) due to a poor level of regulation, as well as low compliance rates pertaining to regulations, the majority of industry professionals have not implemented effectively the generally low standards mandated by the state, including but not limited to disinfection, within which they operate and 3) due to the fact that operators do not screen their clients for infectious diseases, it is critical that operators sterilize their beauty tools, as they are unaware of who has a transmittable condition and 4) although certain high-level disinfection solutions kill the majority of microorganisms, there is no guarantee that the disinfection process will be administered correctly, given the potential for human error regarding the disinfection process and 5) finally, even if the most effective disinfection solutions are used and the disinfection process is administered properly, bacterial spores are not killed by the disinfectants, and evidence indicates that bacterial spores may be spread via beauty tools, creating a need to sterilize in an attempt to eliminate all microorganisms, including bacterial spores.

The decontamination center can have the following components: a closable dedicated soiled storage unit, a sink, a debris-removal unit, a drying center, an enclosing center, a sterilization treatment unit and a closable dedicated sterile storage unit.

The decontamination center can be used to decontaminate beauty tools. For example, the debris removal unit can include a disinfection solution. It is contemplated that beauty tools can be placed within the debris removal unit for approximately 10 minutes.

In another embodiment of the method the decontamination center can be used to sterilize the beauty tools by using a sterilization treatment unit. In another embodiment the debris removal unit, with the disinfection solution and the sterilization treatment unit, can be used together to disinfect and sterilize the beauty tools.

Soiled beauty tools are processed in the decontamination center, forming sterilized beauty tools. The soiled beauty tools can be processed in cassette boxes or individually. Beauty tools that are typically processed in cassette boxes are required for use in a beauty center's most commonly performed treatments. Certain beauty tools are processed through the decontamination center individually, either because they are too small to fit in a cassette box or they are used individually in treatments. These tools include but are not limited to, drill bits, nippers, clippers, metal pushers, one-cuts, tweezers, extractors and scissors. Beauty tools referred to herein can consist of beauty tools processed individually or beauty tools processed in cassette boxes.

The closable dedicated soiled storage unit can be used for containing the soiled beauty tools. The storage unit prevents cross-contamination between soiled and clean or sterile surfaces and materials in the decontamination center.

The decontamination center has a sink, which can be used for flowing water over soiled beauty tools, forming rinsed beauty tools. Beauty tools and cassette boxes are manually sanitized and rinsed prior to immersion in the debris-removal unit with a brush to physically remove visible debris and macro particles. This manual sanitization step of the method. Doing so improves the efficacy of the debris-removal process in the ultrasonic unit.

According to the method, beauty tools are then placed in a debris-removal unit, which can be adjacent to the sink. The debris-removal unit provides ultrasonic cleaning, which plays an important role in the decontamination of beauty tools. Debris-removal is important to ensure the efficacy of the sterilization process of the beauty tools is not reduced or nullified, as the sterilization of a surface can only occur effectively if that surface is free of debris. In an embodiment of the invention, the debris-removal unit can be an area where a debris-removal process is carried out.

The debris-removal unit can have the shape of a tank and can be filled with a cleaning fluid, which can be a cleaner without ammonia, a chemical disinfectant, or combinations thereof, for cleaning the rinsed beauty tools. During treatment in the ultrasonic unit, the cleaning fluid removes macro and micro particles. After the macro and micro particles are removed, cleaned beauty tools are formed.

In another embodiment, the method can comprise the step of disinfecting the rinsed beauty tools instead of processing them in the debris-removal unit. Before the rinsed beauty tools are disinfected, the method includes the step of mechanically removing macro particles from the rinsed beauty tools, forming sanitized beauty tools.

Once the debris-removal step has been completed, the method includes the step of rinsing the cleaned beauty tools with water, forming rinsed and cleaned beauty tools.

The next decontamination step can be drying, which can include a drying basket within the sink for air-drying rinsed beauty tools cleaned in the debris-removal unit. In another embodiment, the decontamination center can have napkins or paper towels to manually dry the cleaned beauty tools.

The next step can be using an enclosing center, which can have a surface and sterilization material for encapsulating the cleaned beauty tools, forming encapsulated cleaned beauty tools. The sterilization material can have an indicator that changes color to indicate when sterilization is complete.

The sterilization material can be a sheet of wrapping paper for wrapping a closable cassette box containing cleaned beauty tools, forming encapsulated clean cassettes boxes containing beauty tools. In an alternative embodiment, the sterilization material can be a plurality of individual pouches for receiving cleaned beauty tools that are processed individually, forming encapsulated clean beauty tools. In another embodiment the cleaned beauty tools can be placed on a flat tray in the sterilization treatment unit without sterilization material.

The next step of the method involves treating the encapsulated beauty tools are treated in a sterilization treatment unit to eliminate completely viral, bacterial and fungal microorganisms. After treatment, sterilized beauty tools are formed.

The method can include storing the sterilized beauty tools in a closable dedicated sterile storage unit, which is used for receiving the sterilized beauty tools. The storage unit ensures that sterile beauty tools remain substantially sterile until their next use.

The method includes using a protocol prohibiting "double dipping" into any products in a beauty center, as doing so can increase the risk of cross-contamination. Therefore, in order to reduce or eliminate the potential for cross-contamination, the method prohibits double-dipping into any products used in beauty centers, such as paraffin wax, hair removal wax, and nail care, skincare, massage and other products.

Two forms of wax are used on a regular basis in salons and spas: paraffin wax and hair removal wax. Paraffin wax is a moisturizing agent applied to the hands, feet or other body parts. It is melted into a liquefied form of wax and is typically stored in a tub. The standard protocol at the majority of beauty centers requires clients to dip their hands or feet, for example, into a communal tub filled with paraffin wax. Once the wax hardens, the client repeats the process multiple times. These wax pots can be a source of cross-contamination of viral, fungal and bacterial microorganisms. The method requires that paraffin be placed in single-use bags, wrapped around a client's hands or feet and disposed of upon completion of the paraffin treatment.

Furthermore, although there are different methods of hair removal, the most commonly used process involves the application of strip wax, wherein technicians smooth wax onto the skin with an applicator, apply a cloth or paper roll on top of the wax and pull on the roll to remove the wax and hair. The waxing process pulls the hair from the root, which commonly result in bleeding. Waxing in the pelvic area routinely results in bleeding. Despite the fact that double-dipping into wax with the same applicator that is used on different clients can cause the cross-contamination of the wax applicator and wax by blood-borne and other pathogens, the majority of salons and spas still double-dip. The method requires beauty center technicians to avoid double-dipping into wax by using a new wooden applicator with each application of wax onto the face or body.

Wax roll-on applicators are also commonly used in salons and spas, wherein wax is applied onto the skin of a client via a roll-on. In doing so, the wax is re-circulated throughout the roll-on. Although most regulatory agencies require roll-ons to be sanitized in between patrons, the wax can still be contaminated with bloodborne and other pathogens once it has been recirculated through the roll-on. Furthermore, the majority of salons and spas do not sanitize and disinfect the roll-on applicators effectively and in between clients. The method requires that roll-on applicators are disposed of after each guest.

It is a common practice for beauty center technicians to dip their hands into products, such as lotions, creams, oils and exfoliating scrubs, while removing them from an uncontaminated container. Hands should never be used to scoop out products. Germs and microbes from the hand can be transferred to the product, which can contaminate the product and lead to the continuous growth of microorganisms in the product. Therefore, the method prohibits double-dipping into nail care, skincare, massage and other products.

The method requires that products be dispensed in such a manner that their removal does not contaminate the remainder of the product in the container. All products are taken out of their packaging by removing a portion of the product from a larger batch of product with a clean beauty tool, such as a spatula. The products can be placed and stored in separate and smaller containers designated for their storage, such as portion-control cups. In addition, certain types of products can be dispensed using specialized dispensers. These methods are equally effective, while providing for safer treatments.

An embodiment of the method can include the step of enclosing the portion-controlled products to prevent contamination of the product. The portion-control cups can be enclosed with a lid or by using plastic wrap to cover the cup. In the alternative, products can be enclosed by placing portions in closable bags.

The embodiment of the method of decontamination requires the use of disposable beauty tools used during beauty treatments that would be damaged or destroyed if disinfected or sterilized, and are therefore, not capable of being disinfected or sterilized. While certain porous beauty tools and supplies can be disinfected or sterilized, the majority are suitable only for one-time use and should be disposed of after they are used on a client because they can not be properly decontaminated. Porous beauty tools are made from an absorbent material that admits the passage of gas or liquids and can harbor bacterial, fungal and viral microorganisms. Disposable beauty tools include, but are not limited to, buffers, high shine buffers, cotton, pedicure shoes, orange wood sticks, foot files, abrasives, toe separators, nail files, wood sticks, plastic spoons, plastic bags, wooden applicators, lancets, and combinations thereof.

The sixth method of decontamination requires the use of a deep cleaning agent to reduce or eliminate the build up of biofilm, which is generated during certain procedures conducted in beauty centers. If not maintained properly, this potentially hazardous film can accumulate on the surface of a pedicure basin, on the internal piping system of a pedicure throne and other surfaces in a beauty center that come into contact with clients and products.

Biofilm naturally occurs in water and forms when bacteria adhere to surfaces in aquatic environments. The bacteria adhere to a slimy, glue-like substance that enables them to anchor to all kinds of materials, including metal and plastic. Biofilm is created from a combination of skin, hair, nail filings, oils, additives, lotions, creams, exfoliating scrubs, wax and residue from a variety of other products used in pedicure and other treatments.

In situations in which biofilm lines a surface, such as the internal piping system of a pedicure station, a disinfectant will only kill microorganisms on the outer layers of the biofilm, but not necessarily microorganisms lining the surface of the piping system. Biofilm reduces or nullifies the efficacy of disinfectants, which cannot kill microorganisms effectively in the presence of debris. Furthermore, it shields microorganisms lurking in water and can act as a breeding ground for certain microorganisms. This holds particularly true for certain water-borne and other pathogens that are resistant to disinfection solution and that are difficult to kill, such as mycobacteria fortuitum.

Biofilm tends to become abundant in nutrient-rich environments and due to its physiological cooperation with aquatic environments, it is inherently more resistant to various antimicrobial treatments and cleaning methods, such as disinfection. Therefore, disinfection alone is not a sufficient method decontamination. It is critical to circulate a deep cleaning agent, such as a chelating surfactant cleaner, in between clients. The surfactant cleaner can be a chelating or non-chelating surfactant cleaner. Chelating surfactants are comprised of a compound of chemicals that degrade and purge the residue that collects on a pedicure basin's surface and the internal pipes of a spa chair so it can be disinfected effectively.

In order to circulate a deep cleaning agent in between patrons, upon completion of the sanitation process, the pedicure basin should be rinsed and filled with fresh water. The deep-cleaning agent should be added to the water and soaked per manufacturer guidelines and the specified time period. If the station is a whirlpool spa chair, the system should be flushed out by turning the jets on. Doing so circulates the deep cleaning agent throughout the internal components of the spa chair. After the specified time period expires, the basin should be drained, rinsed and dried with a clean towel.

The method requires that the pedicure stations be soaked overnight with a deep cleaning agent once a week or as needed, as the extended period of contact between a surface and deep-cleaning agent further aids in the reduction or removal of biofilm.

Upon completion of the sanitation process, the pedicure basin should be rinsed and filled with fresh water. A deep-cleaning agent, such as a chelating surfactant cleaner, should be added to the water and soaked overnight for six to ten hours. If the station is a whirlpool spa chair, the system should be flushed out by turning the jets on per the manufacturer guidelines. Doing so circulates the deep cleaning agent throughout the internal components of the spa chair. The next morning, the system should be flushed by turning the jets on per manufacturer guidelines. Then the basin should be drained, rinsed and dried with a clean towel.

In addition, the pedicure station should be soaked overnight with 10% bleach (1 part bleach to 9 parts water) once per week or on an as needed basis, following the same steps listed in the previous paragraph. This should always be performed the day after the stations are soaked overnight in the deep cleaning agent, as bleach is a more effective decontaminant in the absence of debris or organic matter. As discussed previously, the chelating surfactant cleaner helps reduce biofilm and debris on the internal components of the pedicure station basin and pipes. The combination of soaking the stations overnight in bleach after they soak overnight in a chelating surfactant cleaner aids in the elimination of certain waterborne microorganisms that might be overlooked with disinfection alone.

An embodiment of the method of decontamination includes a set of "rules", also referred as protocols, that consist of a number of hospital-grade standards of infection-control. The first set of protocols can include sanitizing a beauty center technician's and client's hands prior to commencing any treatment. This will eliminate 99.99% of microorganisms. Sanitization can include using waterless gels, sanitizers, soap and water, or water and other cleaning agents.

The second rule can require beauty center technicians to wear gloves during all procedures on customers. Gloves can reduce the potential for cross-contamination from customers to technicians, from technicians to customers, between technicians and between customers.

The "rules" can require the beauty center technicians to wear masks. The masks can be similar to surgical masks, which doctors wear when performing an operation. The masks reduce the potential for cross-contamination.

The "rules" can include the implementation of a ventilation system that reduces odors and chemical vapors for the protection of operators and clients by exhausting those odors and vapors to the outside of the building. The ventilation system will reduce the possibility that people will become ill from fumes and vapors.

An embodiment of the method can include providing related beauty center services. The related beauty center services can include providing drinks, food, bathrobes, towels and combinations thereof. The food and drink can be provided in disposable container. The disposable containers can reduce the possibility that illness will be spread throughout the beauty center.

The embodiment of the method can further include using a protocol for the clean handling of towels, bathrobes, linens and other materials that may come into contact with a customer. The protocol for clean handling can include washing and drying all of the materials that come into contact with a client on-site in a washer and dryer or off-site at a company that specializes in cleaning.

The embodiments of the invention can be better understood with reference to the Figures. FIG. 1 is a flow diagram of the method 100 for decontaminating the beauty center. The embodiment of the method 100 for decontaminating the beauty center includes step 102 using a decontamination center for disinfecting or sterilizing non-disposable beauty tools.

Figure 2:
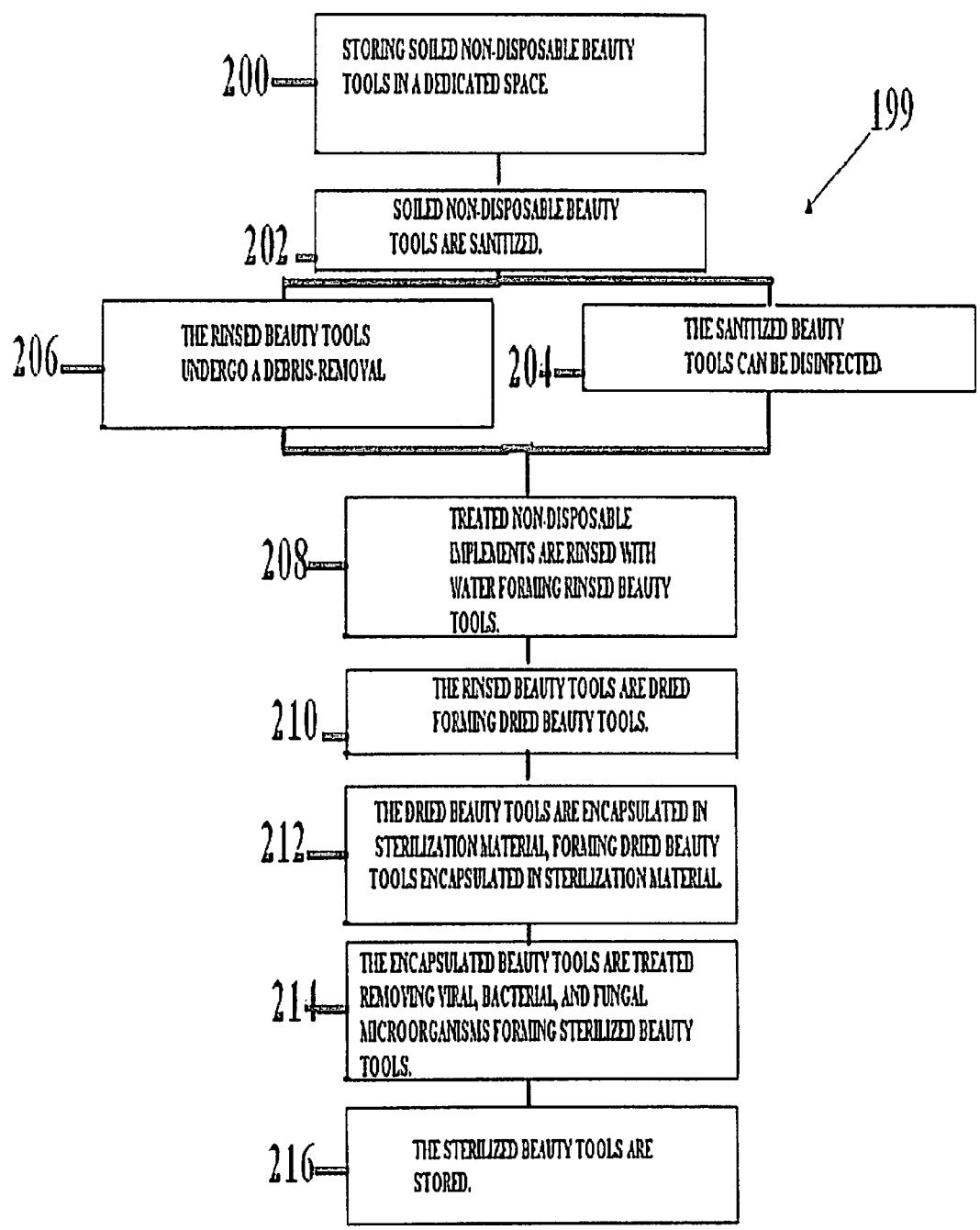
FIG. 2 depicts a flow diagram for an embodiment of the use of a decontamination center.

FIG. 2 depicts the steps of using the decontamination center with regards to sterilizing beauty tools. Step 200 consists of storing soiled non-disposable beauty tools in a dedicated space. Then in step 202, the soiled non-disposable beauty tools are sanitized removing macro particles. After washing, sanitized beauty tools are formed.

In the depicted method step 204, the sanitized beauty tools can be disinfected using Ameri-kleen, which is manufactured by Ameri-kleen Corporation.

Step 206 can be performed in conjunction with step 204 or either step 206 or step 204 can be performed in lieu of the other. In step 206 the rinsed beauty tools undergo a debris-removal, wherein micro particles are removed from the rinsed beauty tools, forming cleaned non-disposable beauty tools. In yet another embodiment, the disinfection of the rinsed beauty tools and the debris-removal can be performed simultaneously.

The cleaned non-disposable beauty tools are rinsed with water in step 208, forming rinsed and cleaned beauty tools. The rinsing should be performed using water at a temperature that will not burn a technician's skin.

In step 210, the rinsed and cleaned beauty tools are dried, forming dried beauty tools. The beauty tools can be air-dried individually or in a closable cassette box. In another embodiment the beauty tools can be dried using towels, napkins or other disposable drying materials.

In step 212, the dried beauty tools are encapsulated in sterilization material, forming dried beauty tools encapsulated in sterilization material.

Then in step 214, the encapsulated beauty tools are treated in a sterilization treatment unit removing viral, bacterial, and fungal microorganisms, forming sterilized beauty tools.

Then in step 216 the sterilized beauty tools are stored in a dedicated space.

Returning to FIG. 1, step 104 depicts the use of disposable beauty tools that are designated for one-time use. Some beauty tools are suitable only for one-time use because they can not be properly and effectively decontaminated. The disposable beauty tools can be buffers, high shine buffers, cotton, pedicure shoes, toe separators, nail files, wood sticks, plastic spoons, plastic bags, wooden applicators, lancets and combinations thereof.

In step 108, a protocol prohibiting double dipping is implemented. Double-dipping can increase the risk of cross-contamination; therefore, the method prohibits double-dipping into any products used in beauty centers, such as paraffin wax, hair removal wax, and nail care, skincare, massage and other products.

In step 110, a disinfectant is used to disinfect surfaces contacted by customers in a spa. The disinfectant can be an EPA-registered, hospital-grade disinfectant, such as Ameri-kleen. Areas requiring disinfection includes nail stations, pedicure stations, manicure bowls or other similar surfaces. Disinfection results in microbal reduction of 99.999%.

In step 112, a deep cleaning agent, such as the surfactant cleaner, is used to reduce or eliminate biofilm generated during procedures by degrading the biofilm. The surfactant cleaner can be First-kleen, manufactured by Ameri-kleen Corporation.

Figure 3:
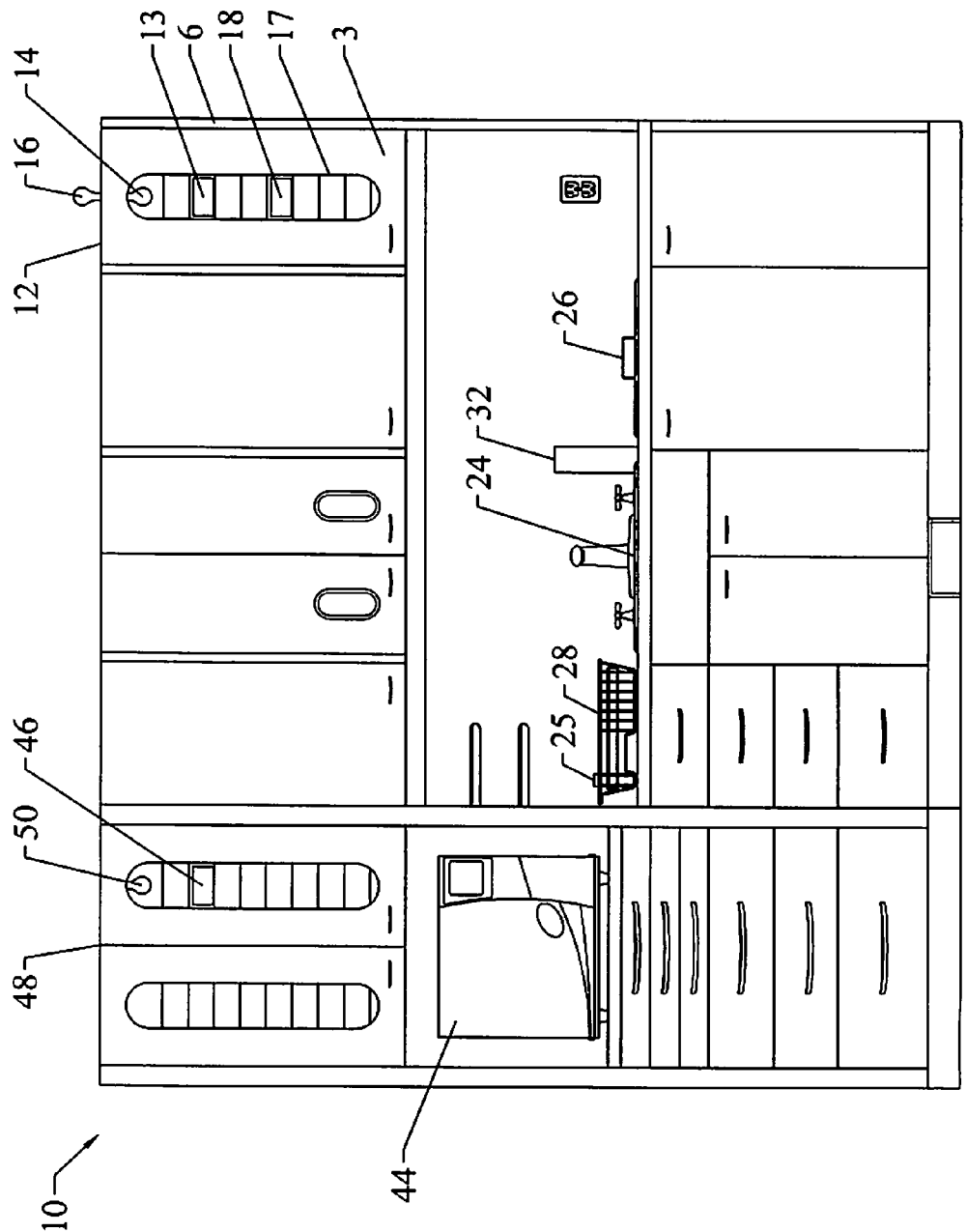
FIG. 3 depicts a schematic of an embodiment of a decontamination center useable with an embodiment of the method.

FIG. 3 depicts a schematic of a beauty center decontamination center 10. In this embodiment, the decontamination center is approximately 8 feet wide, 8 feet high and 3 feet deep.

Starting at the right of FIG. 3, a closable dedicated soiled storage unit 12 is depicted. The closable dedicated soiled storage unit 12 ensures that the soiled beauty tools and cassette boxes do not cross-contaminate any other surfaces or materials in the decontamination center. "Dedicated," as used herein, means that the soiled storage unit 12 is reserved to be used only with soiled tools or cassette boxes 18 containing soiled tools. The soiled beauty tools 13 can be porous or nonporous.

The closable dedicated soiled storage unit 12 is depicted disposed at a raised position above and to the right of the sink 24. The dedicated soiled storage unit 12 can have a width ranging from about ⅓ foot to about 4 feet, a height ranging from about ⅓ foot to about 4 feet and a depth ranging from about ⅓ foot to about 4 feet.

Figure 7:
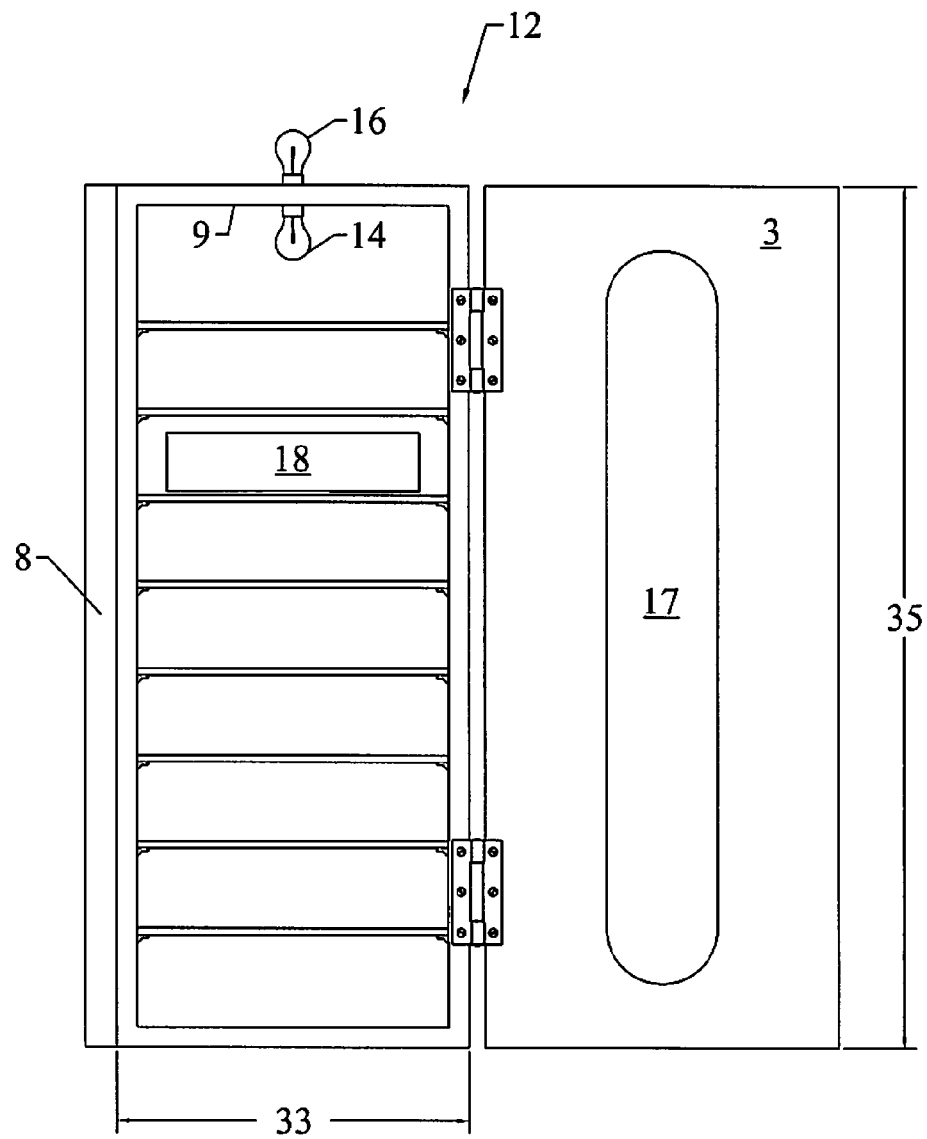
FIG. 7 depicts an embodiment of a closable dedicated soiled storage unit usable with an embodiment of the method.

The dedicated soiled storage unit is best depicted in FIG. 3 and FIG. 7. The closable dedicated soiled storage unit 12 is depicted having a height 35 and width 33. The storage area should have a volume capable of storing at least one closable cassette box or multiple soiled individual beauty tools.

The closable dedicated soiled storage unit 12 has an exterior top with a indicator 16 disposed on it. The dedicated soiled storage unit 12 has an exterior bottom 7, and a first side 6, a second side 8, and a door 3; thereby completely enclosing the soiled storage area 9.

The closable dedicated soiled storage unit 12 is depicted having a door 3 that opens and latches shut. However, in alternative embodiments, the dedicated soiled storage unit can have a lid that creates a snug fit when not removed, a pair of doors that opens and closes using a magnetic means, or a combination thereof.

The closable dedicated soiled storage unit 12 can have an interior light 14, which can be an ultraviolet, infrared light or incandescent light, or a similar means of lighting. The indicator 16 can be a colored light, a color coded flag, a digital display, or a similar means of providing a visual signal that is visible from outside of the soiled storage area.

The indicator 16 is depicted secured disposed on the exterior of the dedicated soiled storage unit dedicated soiled storage unit 12; however, it can be located in other places. The light is powered by a common utility outlet. The light is used to indicate that the closable dedicated soiled storage unit 12 contains soiled beauty tools 13. The indicator 16 is depicted as being visible from outside of the soiled storage area.

The closable dedicated soiled storage unit is also depicted having a viewing panel 17 secured and integrated into the door 3. The viewing panel 17, made of a glass plane, is disposed soiled unit for viewing the soiled beauty tools 13 stored within the dedicated soiled storage unit 12.

It is also contemplated that the viewing panel can be adapted to open by sliding one end toward the opposite end. Also, it can be hinged to the side of the containment chamber, in such a manner that it can be rotatably opened.

Figure 4:
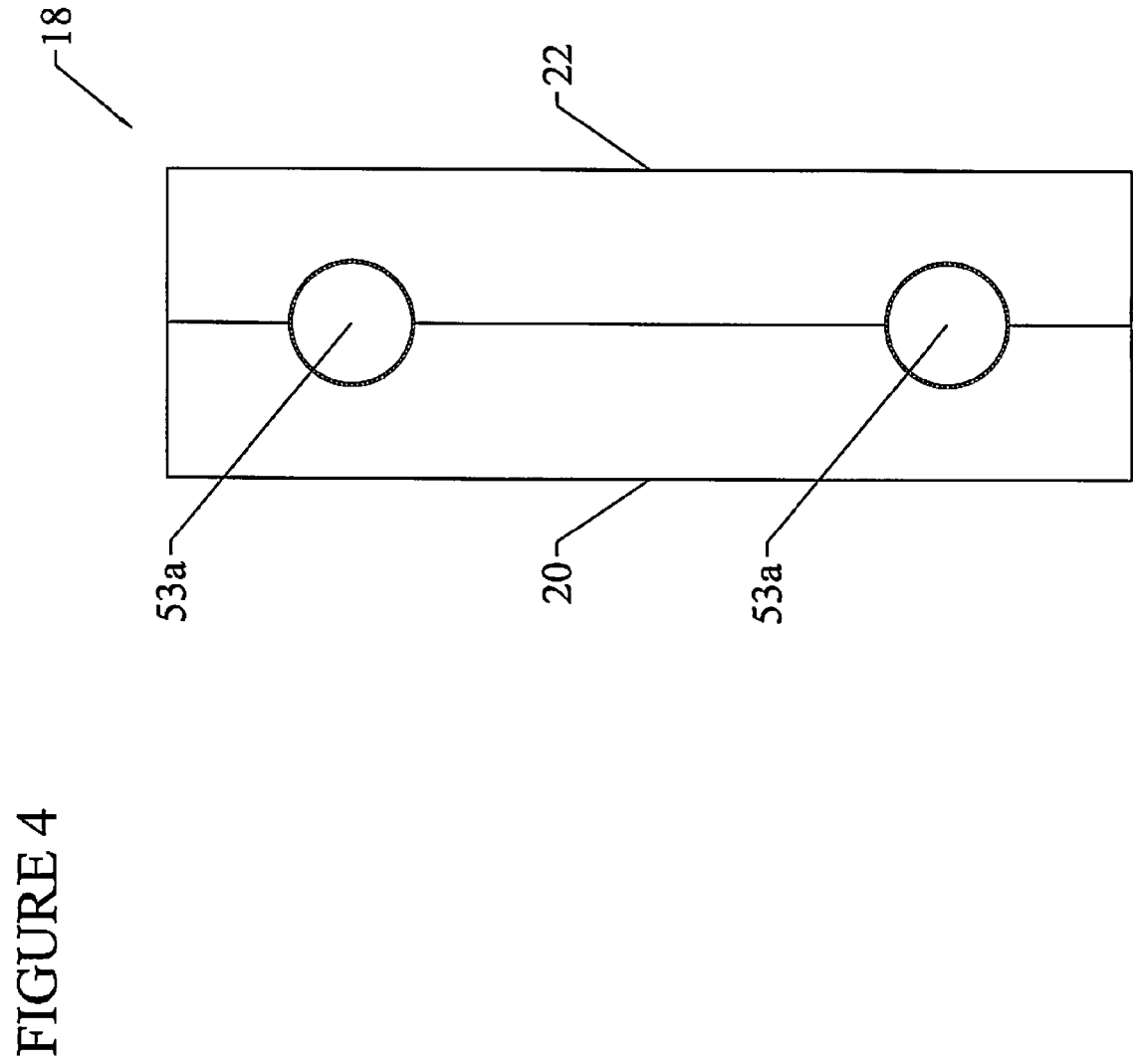
FIG. 4 depicts a side view of an embodiment of a cassette box usable with an embodiment of the method.
Figure 5:
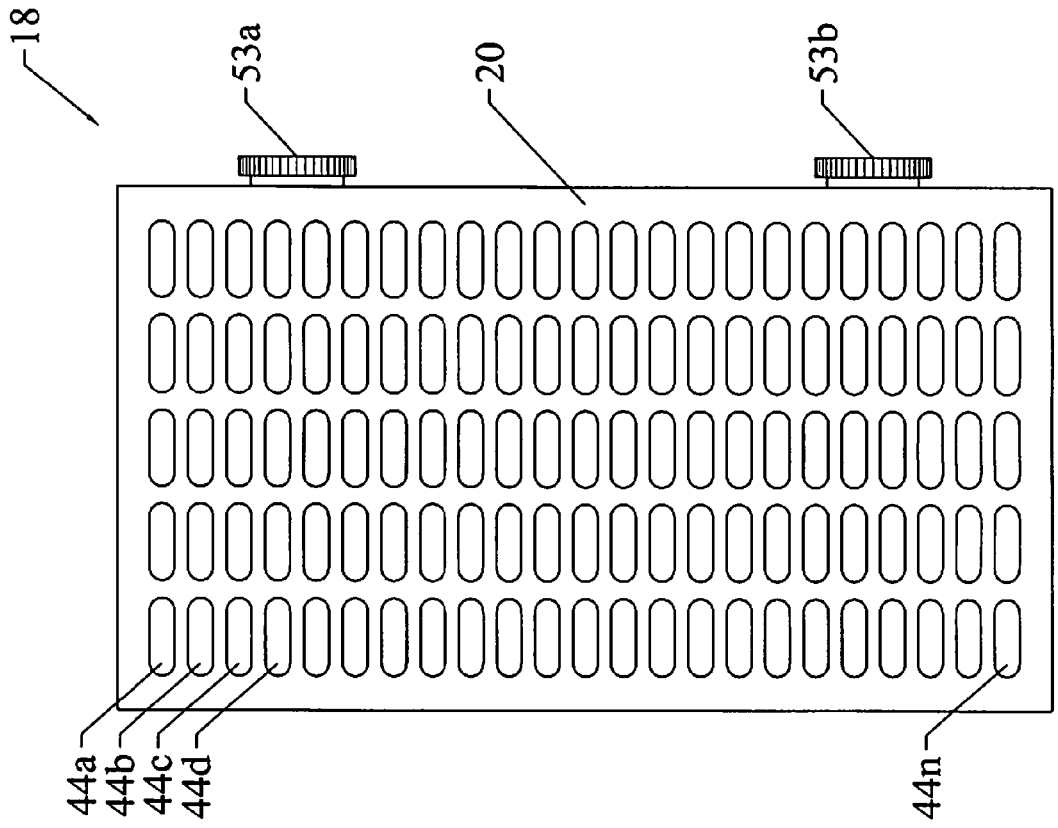
FIG. 5 depicts a top view of an embodiment of a cassette box usable with an embodiment of the method.
Figure 6:
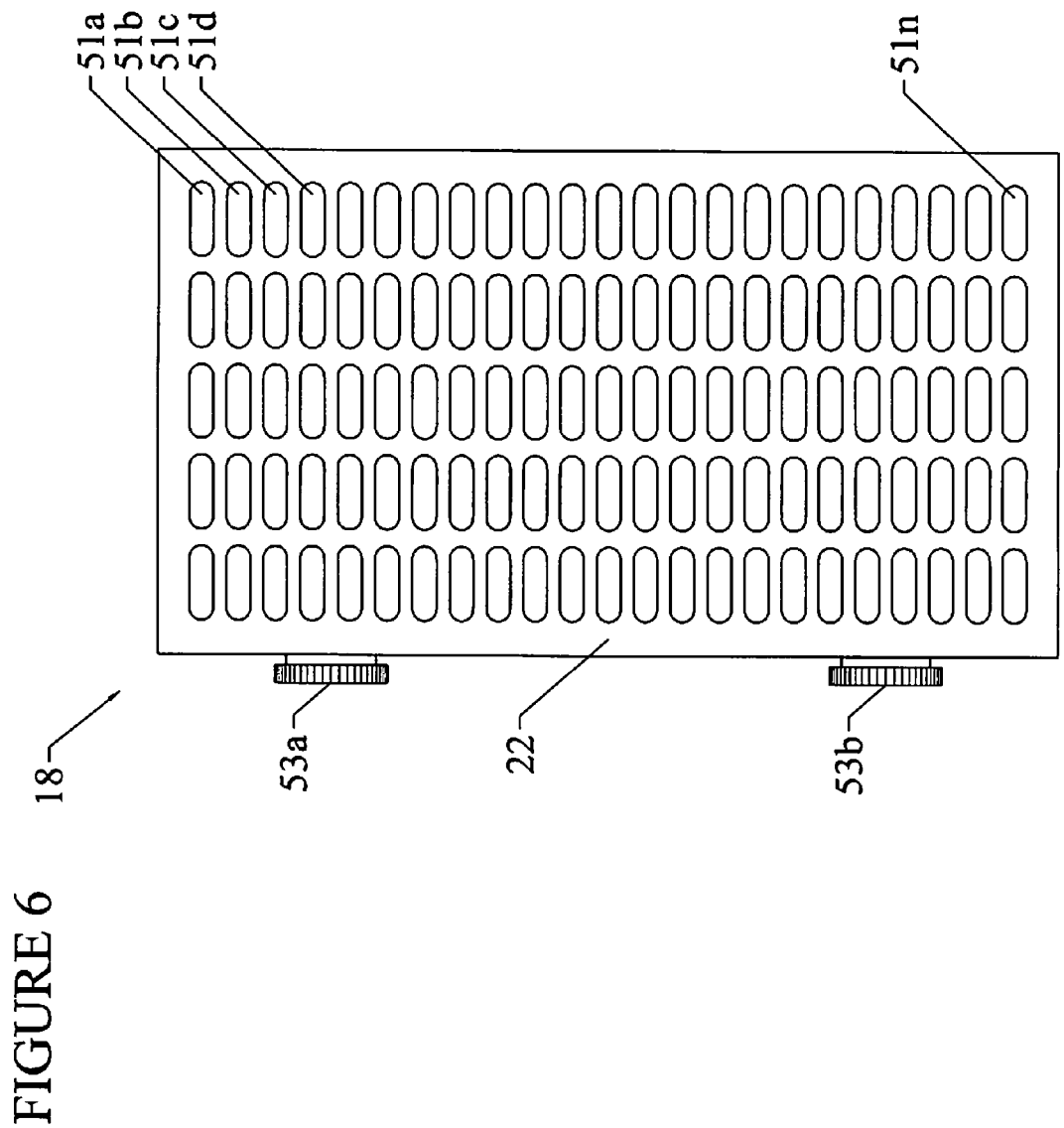
FIG. 6 depicts a bottom view of an embodiment of a cassette box usable with an embodiment of the method.

FIGS. 4, 5 and 6 depict an embodiment of a closable cassette box 18 for containing the soiled beauty tools stored during the sterilization process. FIG. 4 depicts a side view of the closable cassette box 18. The closable cassette box has a perforated top 20 and a perforated bottom 22. The beauty tools are disposed between the perforated top 20 and the perforated bottom 22.

FIG. 5 depicts a top view of the cassette box 18. The perforated top 20 is depicted having a plurality of top openings 44a, 44b, 44c, . . . 44n. The top openings 44a, 44b, 44c, . . . 44n can have a diameter ranging from about 0.10 inches to about 3 inches, and have an elliptical, spherical, circular shape or other similar shape. Locking mechanisms 53a 53b secure the top 20 and bottom 22 together.

FIG. 6 depicts a bottom view of the cassette box 18 depicting the perforated bottom 22 in further detail. The perforated bottom is depicted having a plurality of bottom openings 51a, 51b, 51c, . . . 51n. The bottom openings can be substantially similar to the top openings. In the alternative, the bottom openings can have a different shape, from or a different diameter than the top openings.

Figure 13:
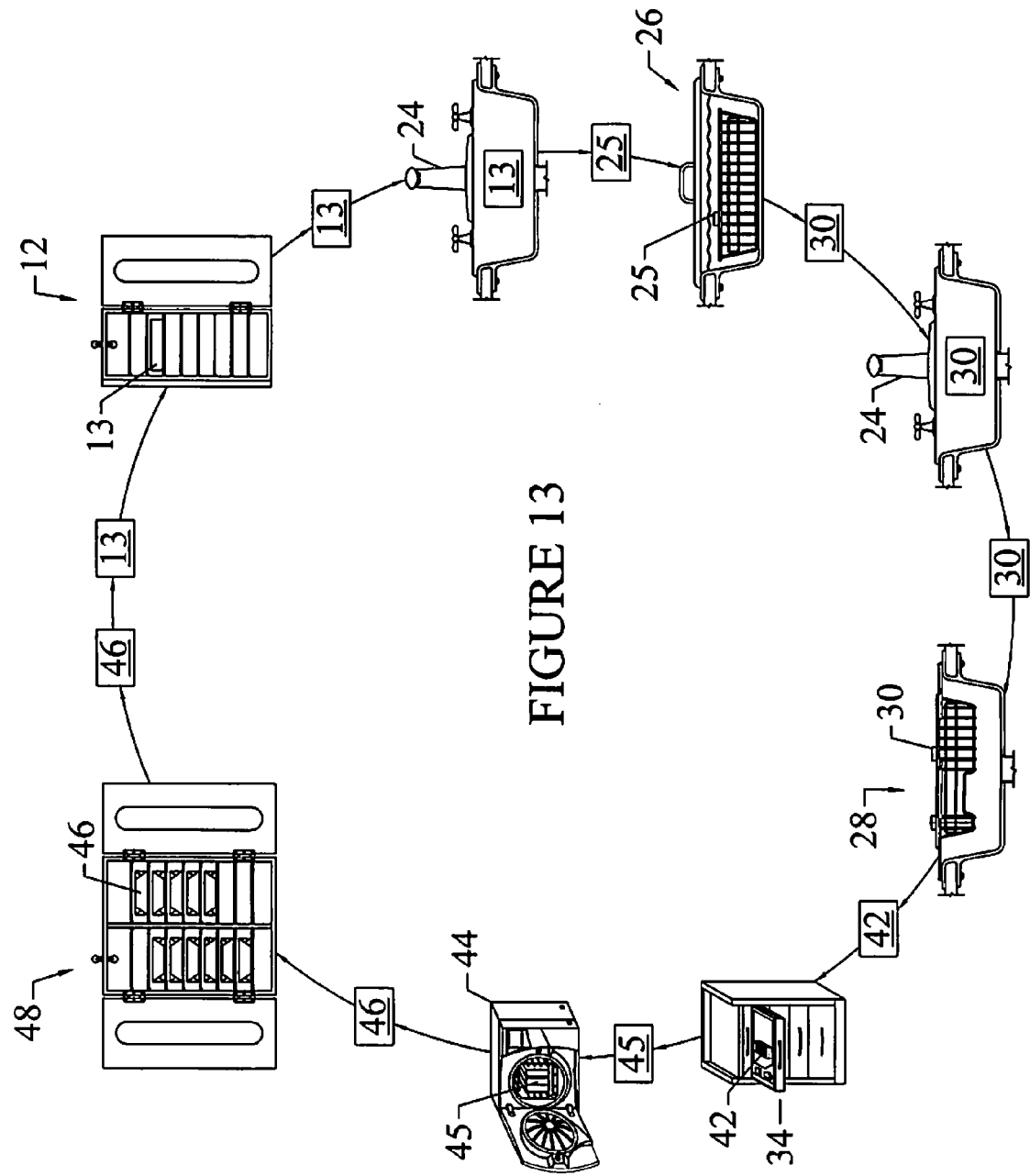
FIG. 13 depicts an embodiment of the flow process of the decontamination center usable with an embodiment of the method.

Turning now to FIG. 3 and FIG. 13. The sink 24, which is used for flowing water over beauty tools and cassettes boxes pre- and post-debris removal, can be a KOHLER® sink. The sink can have a volume ranging from approximately 1 cubic foot to approximately 5 cubic feet. The sink should have a faucet that flows water at a rate of at least 2 gallons/min.

The faucet should also have temperature controls, such as hot and cold dials for flowing hot and cold water. The temperature of the water should flow at a temperature ranging from approximately 60 degrees Fahrenheit to approximately 110 degrees Fahrenheit.

The sink can be adapted for connection to common water mains found in a commercial building. The flowing water is used to remove macro particles, such as skin or nail particles or other debris. After the soiled beauty tools 13 have water flowed over them, rinsed beauty tools 25 are formed.

The embodiment of the decontamination center 10, depicted in FIG. 3, has a debris-removal unit 26, such as an L&R Mfg of Kearney N.J., 50-60 Hz, 400-watt unit. The debris-removal unit 26 provides a cavitation process for removing macro and micro particles, such as skin, dirt and nail particles or other debris. The debris-removal unit can be best seen in FIG. 8.

The debris-removal unit 26 contains a cleaning fluid 27 for treating sanitized beauty tools. The cleaning fluid 27 can be a non-ammoniated general purpose cleaner, a disinfection solution or a similar cleaning fluid. The debris-removal unit 26 can be powered by a common utility outlet or by an alternate power source, such as a battery.

Referring to FIG. 3, the debris-removal unit 26 is depicted adjacent to the sink 24. It is contemplated that in an embodiment of the decontamination center, the debris-removal unit 26 can be at another location proximate to but not adjacent to the sink 24. After the removal of the macro and micro particles in the debris-removal unit, cleaned beauty tools 30 are formed.

The lid is depicted disposed on the top of the debris-removal unit 26 in FIG. 3. The lid should be slightly larger than the debris-removal unit, which allows for convenient insertion of the closable cassette boxes into the chamber.

Figure 8:
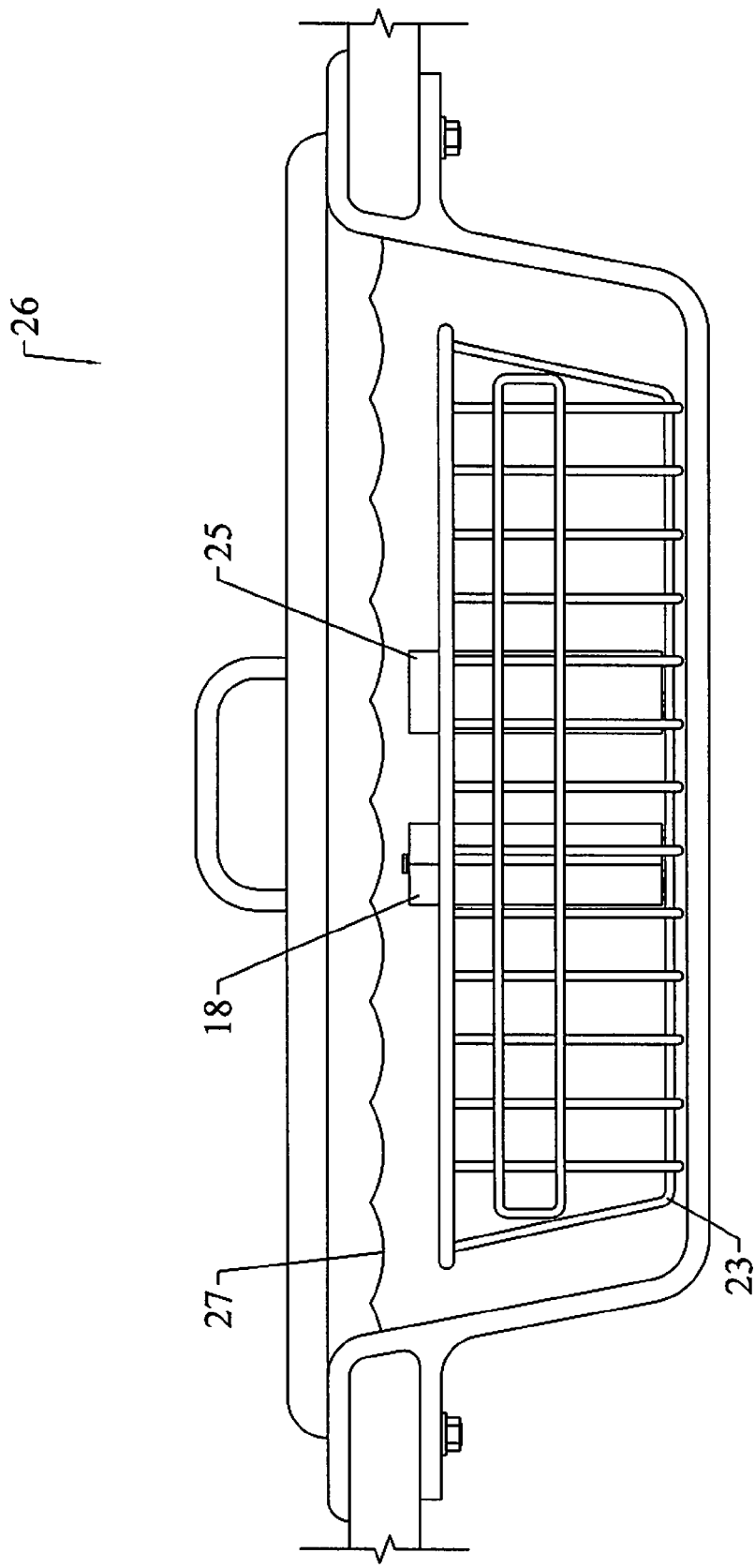
FIG. 8 depicts an embodiment of a debris-removal unit usable with an embodiment of the method.

As shown in FIG. 8, the closable cassette box 18 containing rinsed beauty tools can be fully immersed in the cleaning solution. Placing the cassette box 18 or rinsed beauty tools in a debris-removal basket 23 elevates them from the bottom of the floor of the ultrasonic unit and enables the debris-removal unit's sound waves to be distributed more evenly and consistently around the rinsed beauty tools or the closable cassette box 18, improving the efficacy of the debris-removal process.

Rinsed beauty tools 28 that are processed individually should be placed in the debris-removal unit and fully immersed in the solution. They can be placed directly onto the bottom of the debris-removal unit.

The cleaned beauty tools 30 are then rinsed in the sink 24 after removal from the debris removal unit and placed in the drying center 28. In another embodiment the sink performing the post-debris removal rinsing can be different from the sink performing the post-debris removal rinsing.

A drying center 28, such as a rack, can be disposed adjacent or near to the sink 24 for storing the cleaned beauty tools 30 or closable cassette boxes 18 containing cleaned beauty tools. It is contemplated that the drying center can be adapted to be disposed on a counter top.

The drying center 28 should have an overall area ranging from about 0.5 square foot to about 3 square feet. Towels 32, such as paper towels, cloth towels, or similar towels can be proximate the drying center 28 and used for manually drying the cleaned beauty tools, forming dry cleaned beauty tools 42.

Figure 9:
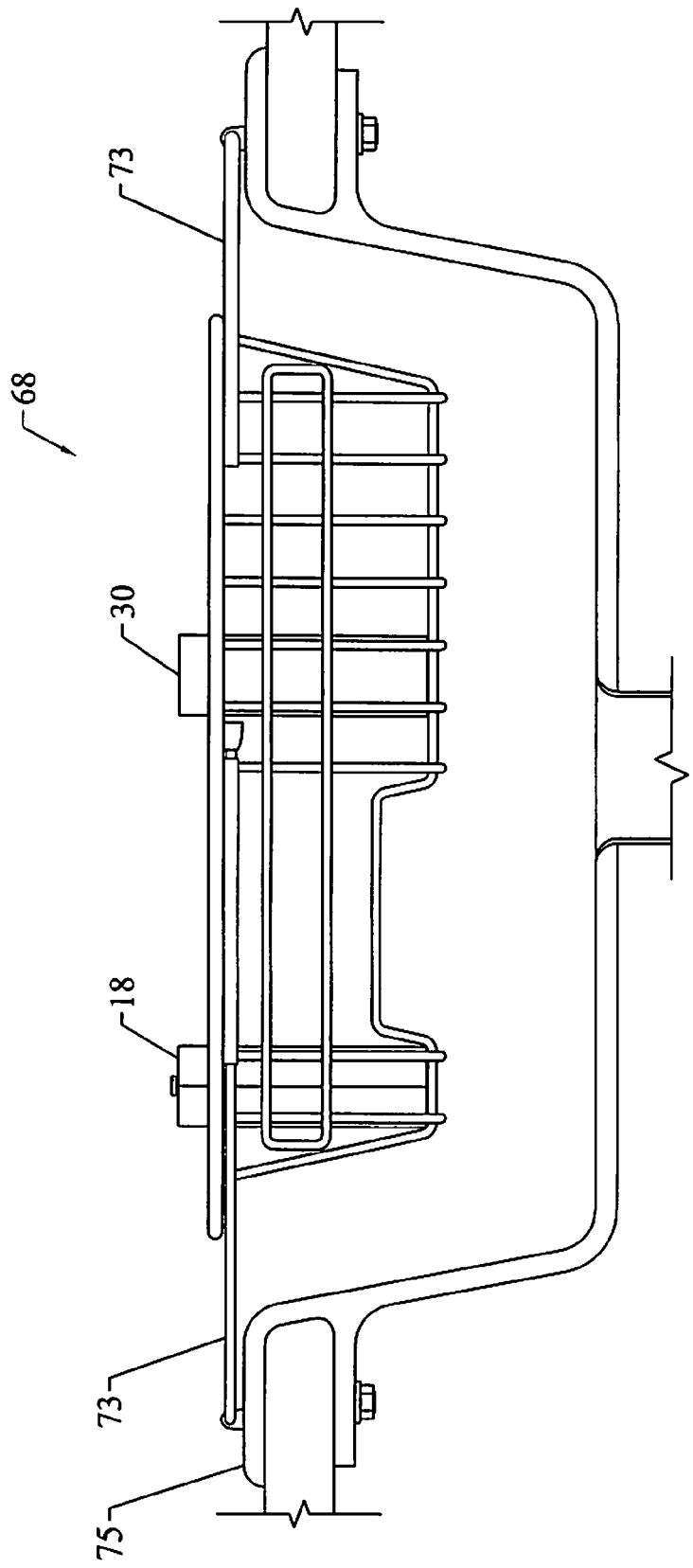
FIG. 9 depicts an embodiment of a drying basket usable with a embodiments of the decontamination center usable with an embodiment of the method.

FIG. 9 depicts an embodiment of a drying basket 68 that is usable with the embodiments of the decontamination center.

In addition to being dried manually, beauty tools and cassette boxes can be air dried in a drying basket 68.

In the depicted embodiment, the drying basket 68 can be an open drying rack, such as a dish drying rack that can be disposed on a flat surface or hung from a sink.

The drying basket 68 is depicted having mounting brackets 73. The mounting brackets can be configured to secure the drying basket to a standard sink basin 75.

The drying basket 68 can be made from stainless steel or another substantially similar hard, nonporous material. The drying basket 68 should have a volume sufficient to contain at least one closable cassette box or several beauty tools.

Figure 10:
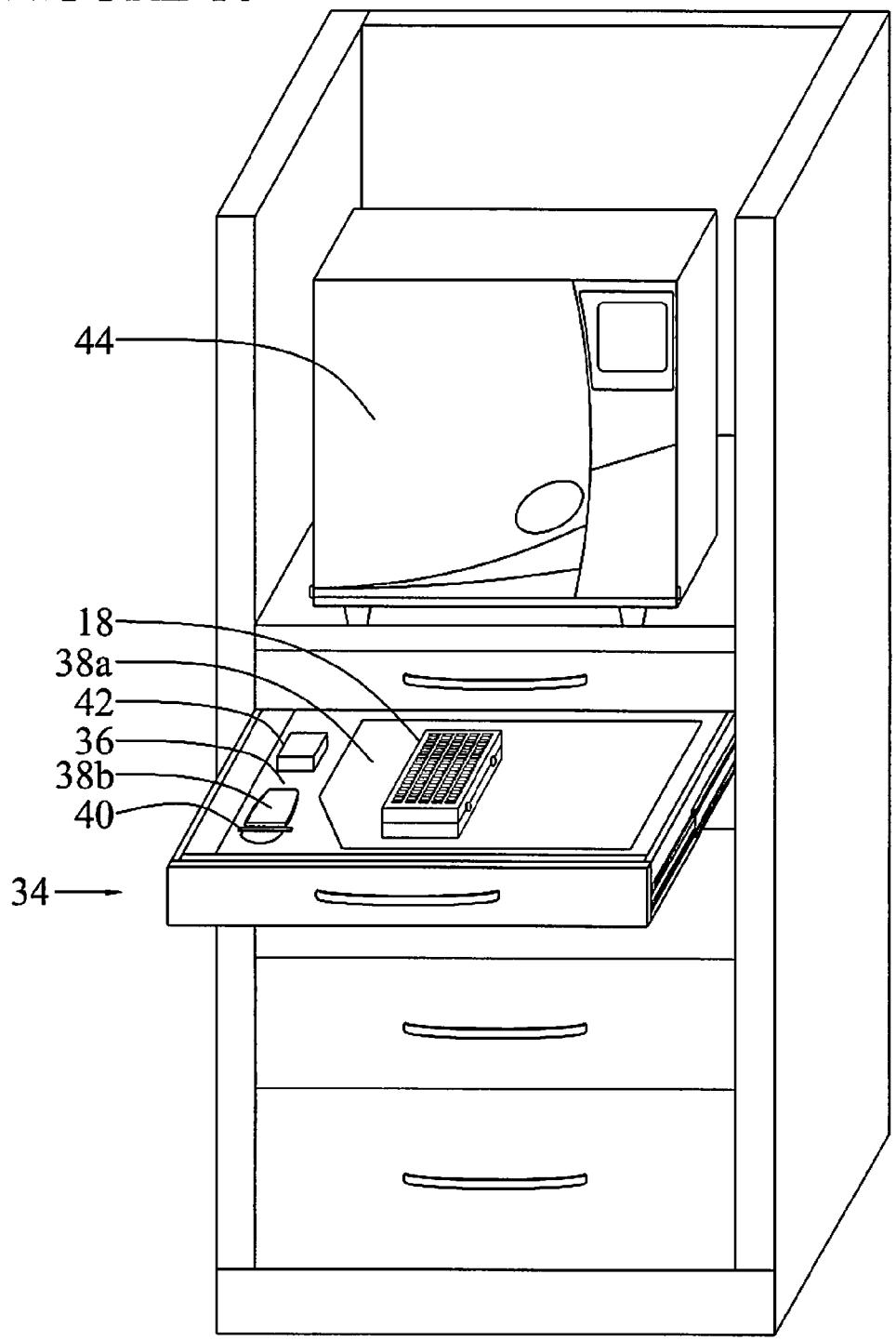
FIG. 10 depicts an embodiment of a enclosing center usable with an embodiment of the method.

Referring now to FIGS. 3, 10, and 13 an enclosing center 34, such as a drawer having a height ranging from about 0.5 foot to about 3 feet, a width ranging from about 0.5 foot to about 3 feet, and a depth ranging from about 0.5 foot to about 3 feet, is depicted disposed proximate to the sink 24.

The enclosing center 34 has a surface 36 and sterilization material 38 for encapsulating the dried clean beauty tools 42 and cassette boxes 18, forming encapsulated clean beauty tools 42 and cassette boxes, as depicted in FIG. 13. The surface can be a drawer in a support unit directly below the sterilization treatment unit 44.

The sterilization material 38 can be a sheet of wrapping paper, and the wrapping paper can be medical-grade for forming encapsulated cassette boxes 18 containing dry clean beauty tools 42.

To form the encapsulated clean beauty tools, the clean beauty tools 42 can be inserted into cassette boxes and wrapped with sterilization material 38a. The paper should be neatly wrapped, as bunched paper can inhibit the efficacy of the sterilization process. The paper is held together with tape that can withhold high levels of heat generated in the sterilization treatment unit. The tape can contain an indicator strip for indicating when sterilization is achieved.

In an alternative embodiment, sterilization pouches 38b are used for receiving the cleaned beauty tools, forming encapsulated clean beauty tools 42. Loose beauty tools are placed in sterilization pouches and sealed in by removing the seal of the adhesive and closing it over the corner of the pouch.

The individual pouches can contain an indicator strip 40 for indicating when sterilization is achieved. The indicator strip 40 can be a heat sensitive strip. The indicator strips change color once they have been processed through a sterilization treatment unit 44 as described below.

The individual pouches can be made of a medical-grade paper on one side, and a transparent polyester film on the other side, which facilitates the identification of beauty tools. These individual pouches are self-sealing, resist tearing, and withstand high temperatures generated in the treatment unit.

Figure 11:
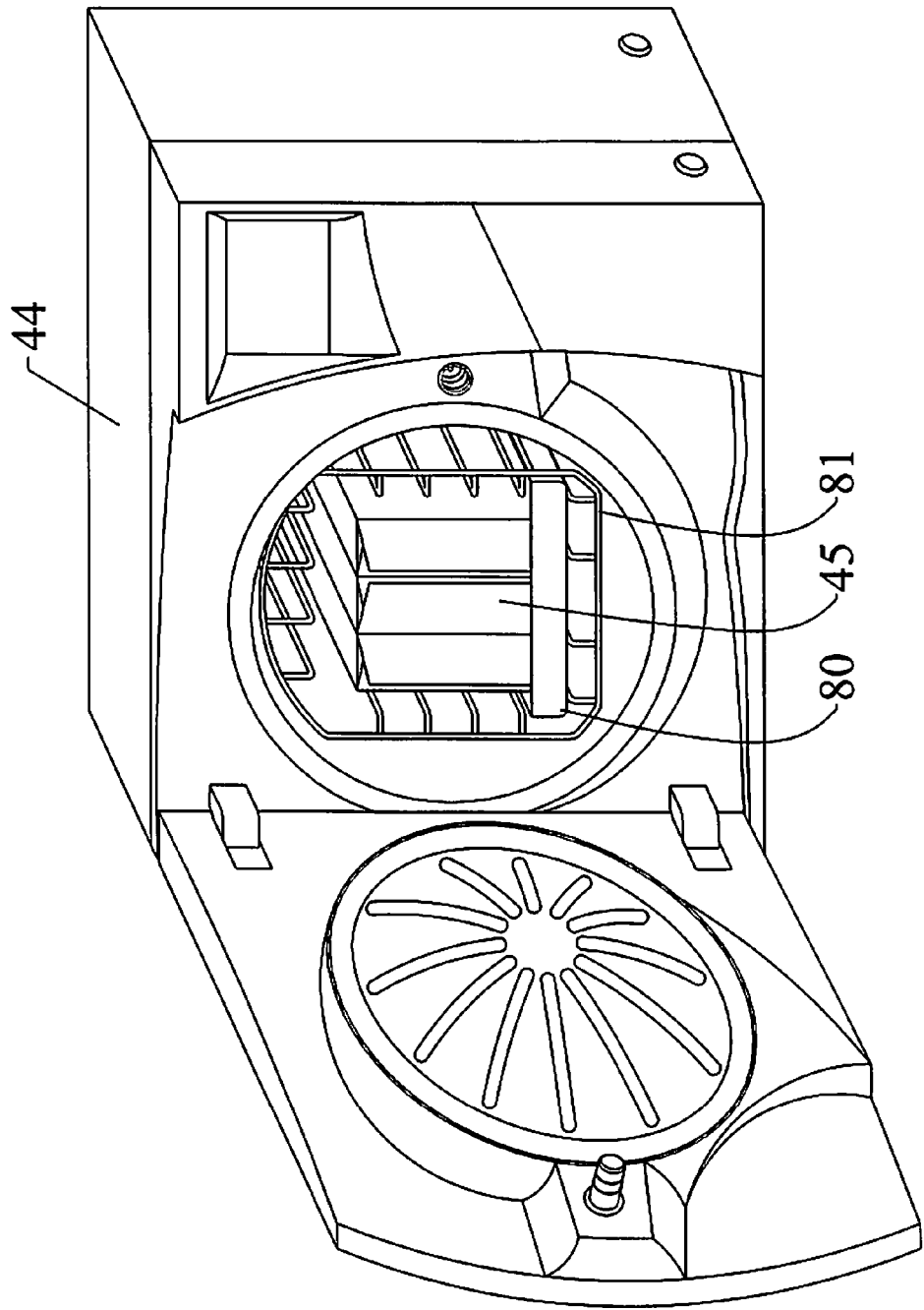
FIG. 11 depicts an embodiment of the sterilization treatment unit usable with an embodiment of the method.

The sterilization unit 44 is depicted in FIGS. 3 and 11. The sterilization treatment unit 44 is for treating the encapsulated cleaned beauty tools or the encapsulated cassette boxes 18 containing the cleaned beauty tools to eliminate viral, bacterial and fungal microorganisms. The encapsulated clean beauty tools 45 can be stored on a tray 80. The tray 80 can slidably engage a rack 81. The sterilization treatment unit 44 can treat at least ten encapsulated clean beauty tools 45 at one time.

After the sterilization treatment unit 44, sterilized beauty tools 46 are formed, as depicted in FIG. 13.

Returning to FIGS. 3 and 11. The sterilization treatment unit 44 can be an autoclave, such as a Lisa autoclave made by A-dec Inc.; a chemiclave, such as Harvey MDT 6000 made by Midmark; a dry heat sterilizer, such as the Cox Dry Heat 110V Sterilizer; an ultraviolet sterilizer; or a gas sterilizer, such as the Anprolene Gas Sterilizer. The sterilization treatment unit 44 can be powered by a common utility outlet or a battery power source.

Figure 12:
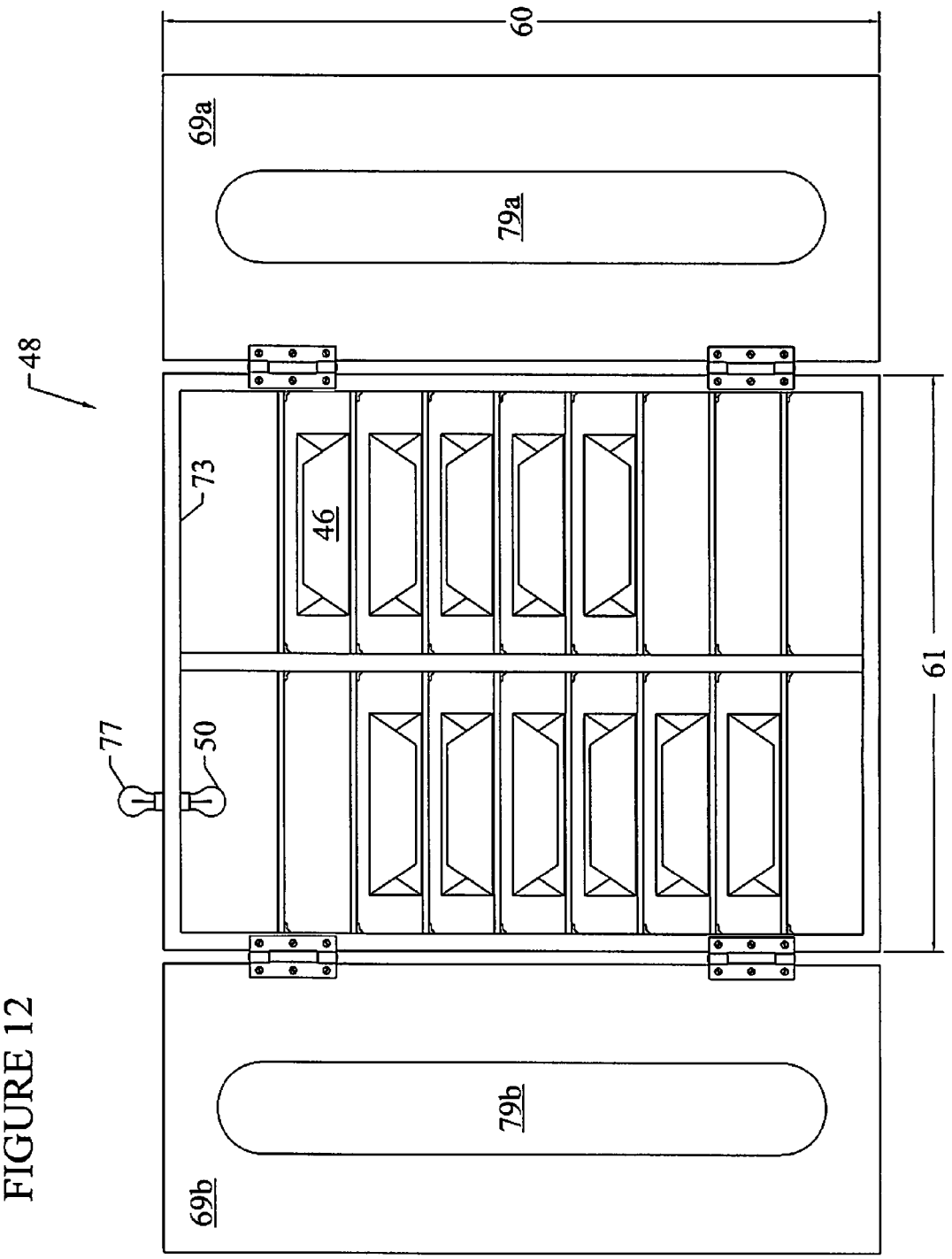
FIG. 12 depicts an embodiment of the closable dedicated sterile storage unit usable with an embodiment of the method.

Referring to FIGS. 3 and 12 an embodiment of a closable dedicated sterile storage unit 48 is depicted. The closable dedicated sterile storage unit 48 is depicted having a storage area 73 for receiving sterilized beauty tools. The closable dedicated sterile storage unit 48 ensures that the sterile beauty tools and cassette boxes remain substantially sterile until their next use. "Dedicated," as used herein, means that the sterile storage unit 48 is reserved to be used only with sterilized tools or cassette boxes 46 containing sterilized tools. The sterilized beauty tools 13 can be porous or nonporous.

The closable dedicated sterile storage unit 48 is depicted disposed at a raised position above and to the left of the sink 24. The dedicated sterile storage unit 48 can have a height ranging from about ⅓ foot to about 4 feet, a width ranging from about ⅓ foot to about 4 feet and a depth ranging from about ⅓ foot to about 4 feet.

The closable dedicated sterile storage unit 48 is depicted having a height 60 and width 61. The storage area should have a volume capable of storing at least one closable cassette box or several beauty tools.

The closable dedicated sterile storage unit 48 has a sterile storage exterior top 63, a sterile storage exterior bottom 64, a first sterile storage side 65, a second sterile storage side 66, a sterile storage back 67 and two doors 69a and 69b.

The closable dedicated sterile storage unit 48 is depicted having two doors 69a and 69b that open and latch shut. However, in alternative embodiments, the dedicated sterile storage unit can have a lid that creates a snug fit when not removed, a pair of doors that opens and closes using a magnetic means, or a combination thereof.

The closable dedicated sterile storage unit 48 can have an interior light 50, which can be an ultraviolet, infrared light or incandescent light, or a similar means of lighting. An indicator 77, which can be a colored light, a color coded flag, a digital display, or a similar means of providing a visual signal that is visible outside of the sterilized storage area, is depicted secured to the first sterile storage side of the closable dedicated storage unit.

However, it can be located in other places. The indicator is powered by a common utility outlet. The light is used to indicate that the closable dedicated sterile storage unit 48 contains sterilized beauty tools. The indicator is visible from outside of the sterile storage area.

The closable dedicated sterile storage unit is also depicted having two viewing panels 79a and 79b. Viewing panel 79a is integrated into door 69a. Viewing panel 79b is integrated into the door 69b.

The viewing panels 79a and 79b, made of a glass plane, are disposed within the doors of the dedicated sterile unit for viewing the sterilized beauty tools stored within the dedicated sterile storage unit 48.

It is also contemplated that the viewing panel can be adapted to open by sliding one end toward the opposite end. Also, it could be hinged to the side of the containment chamber, in such a manner that it can be rotatably opened.

The containment chamber of the closable dedicated sterile storage unit 48 is depicted with a side 65 that includes a hinged door 66a that is secured by the use of a latch 67a.

The embodiments of the decontamination center provide a compact, efficient and effective way to ensure that beauty tools are kept in a sanitary condition. This is important because if the process is not efficient and effective, many tools will be reused without proper decontamination, which can lead to the spread of communicable diseases.

While these embodiments have been described with emphasis on the embodiments, it should be understood that within the scope of the appended claims, the embodiments might be practiced other than as specifically described herein.

What is claimed is:

1. A method for decontaminating a beauty center comprising:
   a. using a sterilization center with connected components for decontaminating soiled non-disposable beauty tools, wherein the use of the sterilization center comprises in order:
      i. storing soiled non-disposable beauty tools in a dedicated space;
      ii. removing particles from the soiled non-disposable beauty tools by performing a step of:
         (a) removal of macro-particles from the soiled non-disposable beauty tools by mechanical scrubbing;
      iii. rinsing the cleaned non-disposable beauty tools with water to form cleaned and rinsed beauty tools;
      iv. drying the cleaned and rinsed beauty tools to form dried beauty tools;
      v. enclosing the dried beauty tools in sterilization material to form enclosed dried beauty tools;
      vi. removing viral, bacterial and fungal microorganisms from the enclosed dried beauty tools by treating the enclosed dried beauty tools in a sterilization treatment unit to form sterilized beauty tools; and
      vii. storing the sterilized beauty tools in a dedicated space;
   b. using disposable beauty tools in conjunction with the non-disposable beauty tools in the beauty center;
   c. using a protocol prohibiting "double dipping" with products in the beauty center;
   d. using a disinfectant to disinfect surfaces contacted with customers in the beauty center;
   e. using a deep-cleaning agent to reduce or eliminate biofilm generated during procedures performed in the beauty center; and
   f. wherein during (ii), a step of removal and loosening of macro and micro-particles from soiled non-disposable beauty tools using an ultrasonic debris-removal unit is performed directly prior to step (a), or directly after step (a).

2. The method of claim 1, wherein at least one of several types of microorganisms are terminated using the method.

3. The method of claim 2, wherein the step of debris-removal comprises using a chemical to assist in the removal of the micro-particles.

4. The method of claim 3, wherein the chemical is a member of the group consisting of: a cleaner without ammonia, a chemical disinfectant, a general purpose cleaner, and combinations thereof.

5. The method of claim 1, further comprising implementing a ventilation system for exhausting fumes and vapors.

6. The method of claim 1, wherein the disposable beauty tools are a member of the group consisting of buffers, high shine buffers, cotton, pedicure shoes, toe separators, nail files, wood sticks, plastic spoons, plastic bags, applicators, sanding bands, brushes, lancets, and combinations thereof.

7. The method of claim 1, wherein the step of using a protocol prohibiting "double dipping" further comprises the step of dispensing products with a clean tool or specialized dispenser to avoid double dipping with products in the beauty center, forming portion-controlled products.

8. The method of claim 1, wherein the step of using a protocol prohibiting "double dipping" further comprises the step of placing paraffin wax into a single-use disposable bag.

9. The method of claim 1, wherein the step of using a protocol prohibiting "double dipping" further comprises the step of using a new applicator every time hair removal wax is extracted from a wax pot.

10. The method of claim 1, wherein the step of using a protocol prohibiting "double dipping" further comprises the steps of disposing of a roll-on applicator after each use.

11. The method of claim 1, wherein the deep-cleaning agent is a surfactant cleaner.

12. The method of claim 11, wherein the surfactant cleaner is a chelating or non-chelating cleaner.

13. The method of claim 1, further comprising using a protocol comprising a member of the group consisting of:
   a. wearing gloves by the beauty center technician during all procedures on customers;
   b. sanitizing hands of the beauty center technician and customers;
   c. wearing masks by the beauty center technician; and
   d. combinations thereof.

14. The method of claim 1, further comprising providing related beauty center services to customers with the method, including providing a member of the group: drinks, food, linens, and combinations thereof.

15. The method of claim 14, further comprising the step of using disposable containers for the food and drinks to reduce the possibility of spreading diseases at the beauty center.

16. The method of claim 14, wherein the protocol prohibiting double dipping further comprises using a protocol for the clean handling of towels, bathrobes, sheets and other items that contact a technician or customer.

17. The method of claim 1, wherein the step of drying rinsed beauty tools further comprises air-drying or manually drying the cleaned beauty tools, wherein the clean beauty tools can be air-dried or manually dried individually or in a closable cassette box.

18. The method of claim 1, wherein the step of using a sterilization center for decontaminating soiled non-disposable beauty tools comprises sanitizing the beauty tools prior to sterilizing the beauty tools.

* * * * *